(12) United States Patent
Nishio et al.

(10) Patent No.: US 7,547,379 B2
(45) Date of Patent: Jun. 16, 2009

(54) RESPONSIVE GLASS MEMBRANE FOR ION SELECTIVE ELECTRODE AND ION SELECTIVE ELECTRODE

(75) Inventors: Yuji Nishio, Kyoto (JP); Yasukazu Iwamoto, Kyoto (JP); Tadanori Hashimoto, Tsu (JP)

(73) Assignees: Horiba, Ltd., Kyoto (JP); Mie University, Mie (JP)

( * ) Notice: Subject to any disclaimer, the term of this patent is extended or adjusted under 35 U.S.C. 154(b) by 0 days.

(21) Appl. No.: 12/037,745

(22) Filed: Feb. 26, 2008

(65) Prior Publication Data

US 2008/0207428 A1 Aug. 28, 2008

(30) Foreign Application Priority Data

Feb. 26, 2007 (JP) ............................. 2007-045805

(51) Int. Cl.
*G01N 27/333* (2006.01)
*G01N 27/36* (2006.01)

(52) U.S. Cl. ...................... 204/420; 204/416; 204/419; 204/433; 204/435

(58) Field of Classification Search ................ 204/435, 204/433, 416, 419, 420; 501/46
See application file for complete search history.

(56) References Cited

U.S. PATENT DOCUMENTS

| | | | | |
|---|---|---|---|---|
| 4,282,079 | A * | 8/1981 | Chang et al. | ................. 204/420 |
| 6,485,622 | B1 * | 11/2002 | Fu | .............................. 204/421 |
| 2005/0034984 | A1 * | 2/2005 | Iwamoto et al. | ............. 204/420 |
| 2005/0082167 | A1 * | 4/2005 | Iwamoto et al. | ............. 204/433 |
| 2008/0206547 | A1 * | 8/2008 | Nishio et al. | ............. 428/319.1 |

* cited by examiner

*Primary Examiner*—Bruce F Bell

(57) ABSTRACT

The present claimed invention intends to provide a responsive glass membrane for ion selective electrode glass and an ion selective electrode comprising the responsive glass membrane that produces a self-cleaning function when the ultraviolet rays are irradiated although no change is brought in a composition of a sample solution as being an object to be measured and that is low in electric resistance value and superior in responsivity under an ordinary measurement environment.

The responsive glass membrane for ion selective electrode is made of the titanium-containing oxide glass that contains 20~80 mol % of titanium dioxide and lithium oxide.

17 Claims, 6 Drawing Sheets

RESPONSIVE GLASS MEMBRANE FOR ION SELECTIVE ELECTRODE AND ION SELECTIVE ELECTRODE

BACKGROUND OF THE INVENTION AND RELATED ART STATEMENT

The present claimed invention relates to a responsive glass membrane for ion selective electrode having a self cleaning function and an ion selective electrode comprising the responsive glass membrane.

Conventionally, it has been known that crystalline titanium dioxide ($TiO_2$, titania) of rutile type or anatase type has photocatalytic activity. Powerful oxidation-reduction properties and superhydrophilic properties are represented as the photocatalytic activity; disinfection treatment is applied to a wall or a floor of a surgery room in a hospital by coating the wall or the floor with titanium dioxide and irradiating it with the ultraviolet radiation by making use of the oxidizing properties of superoxide ion formed in the degradation of $H_2O$, antifog treatment is applied to a side mirror of an automobile or a mirror on a road by coating the mirror with titanium dioxide so that self cleaning can be conducted when it rains by making use of the superhydrophilic properties, or the superhydrophilic properties is also applied to taint prevention of an exterior wall of a building or a sheet for a tent.

The responsive glass membrane of the ion selective electrode such as a pH electrode is usually made of silicate glass, and it requires sufficient washing by the use of distilled water or the like every time measurement is conducted in order to keep an accuracy of the measurement. In addition, it requires calibration of pH or the like after washing.

With the view to these properties, if the photocatalytic activity of titanium dioxide can be utilized for the responsive glass membrane, it is considered that the responsive glass membrane can be easily washed and that an ion selective electrode requiring no calibration can be obtained as well.

However, if the photocatalytic activity is given to the responsive glass membrane of the ion selective electrode by crystalline titanium dioxide, an electrical potential fluctuation might occur due to generation of hydroxyl by the superhydrophilic properties, oxidization properties might be performed on a sample solution as being an object to be measured so as to degrade or change its component. As a result of this, it has not been tried that titanium dioxide is applied to the responsive glass membrane with intent to give the photocatalytic activity.

In addition, if a concentration of lithium oxide in the glass is high, it is alleged that an electric resistance decreases in general. As a result, if the glass containing a lot of lithium oxide is used for the responsive glass membrane of the ion selective electrode, there is a possibility that varieties of effects due to low electric resistance can be obtained; for example, response is improved, no necessity to use expensive materials such as Teflon (registered trademark) for connectors because high insulation properties is not required for electric wiring sections and some dust may be permitted in an assembling environment, in addition to a self cleaning effect because of titanium dioxide.

Then the present claimed invention intends to provide a responsive glass membrane for ion selective electrode glass and an ion selective electrode comprising the responsive glass membrane that produces a self-cleaning function when the ultraviolet rays are irradiated although no change is brought in a composition of a sample solution as being an object to be measured under an ordinary measurement environment and that is low in electric resistance value and superior in sensitivity.

SUMMARY OF THE INVENTION

More specifically, the responsive glass membrane for ion selective electrode in accordance with the present claimed invention is a responsive glass membrane for ion selective electrode made of oxide glass and is characterized by that the oxide glass contains 20~80 mol % of titanium dioxide and lithium oxide.

Recently, it is reported that amorphous titanium dioxide also produces photocatalytic activity ("Hikari alliance" (Light alliance) March, 2004, 13~17), however, the photocatalytic activity is extremely weak so that practical application of the amorphous titanium dioxide has not been tried with intent to photocatalytic activity.

However, the present claimed inventor has newly found that photocatalytic activity that can be for practical use can be induced by irradiating the ultraviolet rays on amorphous titanium dioxide so that the present claimed invention is perfected.

Since the responsive glass membrane for ion selective electrode in accordance with this invention is made of the oxide glass (hereinafter also called as the titanium-containing oxide glass) containing high concentration of titanium dioxide, although no photocatalytic effect is produced at a time of measuring the pH, photocatalytic activity is induced by irradiating the ultraviolet rays at a time of washing so that organic matters attached to the responsive glass membrane is degraded by the oxidizing effect, and the self cleaning function can be produced by the superhydrophilic effect so that the taint attached to the responsive glass membrane is easily detached. As a result of this, the responsive glass membrane can be kept in a clean state easily, which enables a highly accurate measurement on a constant basis. In addition, since there is no need of washing the responsive glass membrane by the use of distilled water, calibration also becomes unnecessary. As a light source for the ultraviolet rays, for example, an LED, a hydrogen discharge lamp, a xenon discharge lamp, a mercury lamp, a ruby laser, a YAG laser, an excimer laser or a dye laser is used.

The contained amount of titanium dioxide in the titanium-containing oxide glass used in this invention is 20~80 mol %, however, if it is less than 20 mol %, the photocatalytic activity induced by the irradiation of the ultraviolet rays is weak and insufficient for self cleaning of the responsive glass membrane and if it is over 80 mol %, it is impossible to manufacture the glass with an ordinary melting method.

In addition, if the above-mentioned specified amount of titanium dioxide is contained, a radius of Ti ion of the titanium-containing oxide glass is about one and a half times of a radius of Si ion. If an ion conductive material is mixed, it is possible to maintain the mobility of a lithium ion ($Li^+$) at a higher level and to obtain the glass having less resistance value.

Furthermore, the titanium-containing oxide glass is superior in corrosion resistance because it contains titanium dioxide of a higher concentration.

The responsive glass membrane for ion selective electrode has to be ionic conductive, however, since the titanium-containing oxide glass contains lithium oxide, it can show a preferable ionic conductive through $Li^+$. The containing amount of lithium oxide is preferably 1~50 mol %, and more preferably, about 25~30 mol %. If it is less than 1 mol %, the ionic conductive is insufficient. If it is over 50 mol %, the corrosion resistance is deteriorated.

More specifically, if the titanium-containing oxide glass contains 1~50 mol % of lithium oxide, it can show the ionic conductive that is preferable for being used for the responsive glass membrane for ion selective electrode through $Li^+$.

The oxide glass used in the present claimed invention may be either one of phosphate glass, silicate glass and borate glass. Titanophosphate glass containing 1~50 mol % of lithium oxide is more preferable of all.

If titanophosphate glass is used for the responsive glass membrane for ion selective electrode, it is possible to trim weight of the ion selective electrode itself and to improve the response because it is low in electric resistance as well. In addition, it is possible to flexibly set the distortion in consideration of mechanical strength and to extremely improve the flexibility in designing the responsive glass membrane because the responsive glass membrane is low in electric resistance. Furthermore, since titanium dioxide exists in a glassy (amorphous) state whose photocatalytic activity is low, the photocatalytic activity will hardly cause a negative effect on the measurement itself or a sample solution at a time of measuring an ionic concentration, and self cleaning function is produced because the photocatalytic activity is induced only at a time of irradiating the intense ultraviolet rays intentionally in order to wash the responsive glass membrane.

As a result of this, if the titanophosphate glass is used for the responsive glass membrane, the responsive glass membrane can be made very low in electric resistance (lower at two digits in resistivity than that of a conventional responsive glass membrane) with producing the self cleaning function due to titanium dioxide.

The titanium-containing oxide glass may contain cesium oxide ($Cs_2O$). This can reinforce the ionic conductive by the lithium ion.

Furthermore, the titanium containing oxide glass may contain oxidative product of the group 3 element such as oxidized scandium ($Sc_2O_3$) or yttrium oxide ($Y_2O_3$). This can stabilize the lithium ion, reduce a thickness of hydrated gel layer and improve response.

In addition, if oxidized lanthanum ($La_2O_3$) is mixed as the oxidative product of the group 3 element, it is possible to reduce the alkali error.

Furthermore, if barium oxide (Bao) is mixed into the titanium-containing oxide glass, it is possible to restrain the alkali response.

The responsive glass membrane for ion selective electrode in accordance with the present claimed invention is manufactured by weighing/mixing and then melting a raw material of the titanium-containing oxide glass, followed by cooling. In this case, after the raw material is melted, the glass expresses black because of residual $Ti^{3+}$. Then annealing is provided at 200~1000° C. for more than one day so as to transform $Ti^{3+}$ into $Ti^{4+}$. As a result, the glass becomes transparent. In addition, $Ti^{3+}$ may be intentionally left in order to lower a value of the electric resistance of the glass.

The ion selective electrode comprising the responsive glass membrane for ion selective electrode of the present claimed invention is also one of the present claimed inventions. More specifically, the ion selective electrode is an ion selective electrode comprising a responsive glass membrane made of oxide glass, and is characterized by that the oxide glass contains 20~80 mol % of titanium dioxide and lithium oxide.

In accordance with this invention, it is possible to obtain a responsive glass membrane that produces self cleaning function because photocatalytic activity is induced by irradiating the ultraviolet rays at a time of washing although it shows no photocatalytic activity at a time of measurement. As a result of this, it is possible to clean the ion selective electrode easily without having an influence on a sample solution as being an object to be measured and to conduct a stable measurement with high accuracy with less contamination or less influence of residual material. In addition, since there is no need of washing by the use of distilled water like a conventional ion selective electrode, calibration also becomes unnecessary, thereby enabling to conduct measurement continuously and to obtain a stable and continuous measurement result with high accuracy.

In addition, the electric resistance also can be reduced if the titanophosphate glass containing lithium oxide of high concentration is used as the responsive glass membrane.

DETAILED DESCRIPTION OF THE PREFERRED EMBODIMENTS

A pH glass electrode as being an ion selective electrode in accordance with one embodiment of the present claimed invention will be explained with reference to drawings.

Figure 1:
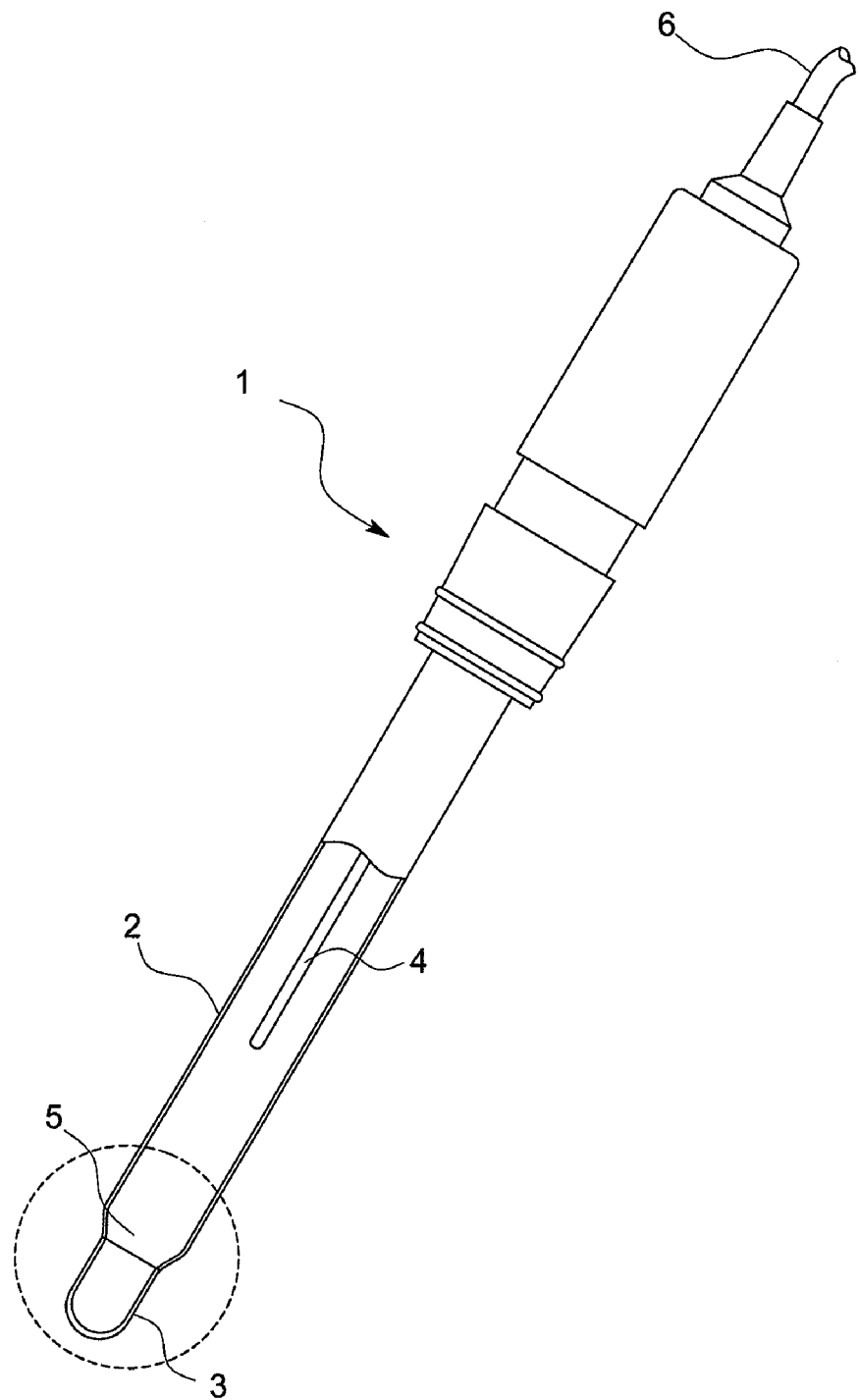
FIG. 1 is a partially broken view showing a part of an internal structure of a pH glass electrode in accordance with one embodiment of the present claimed invention.
Figure 2:
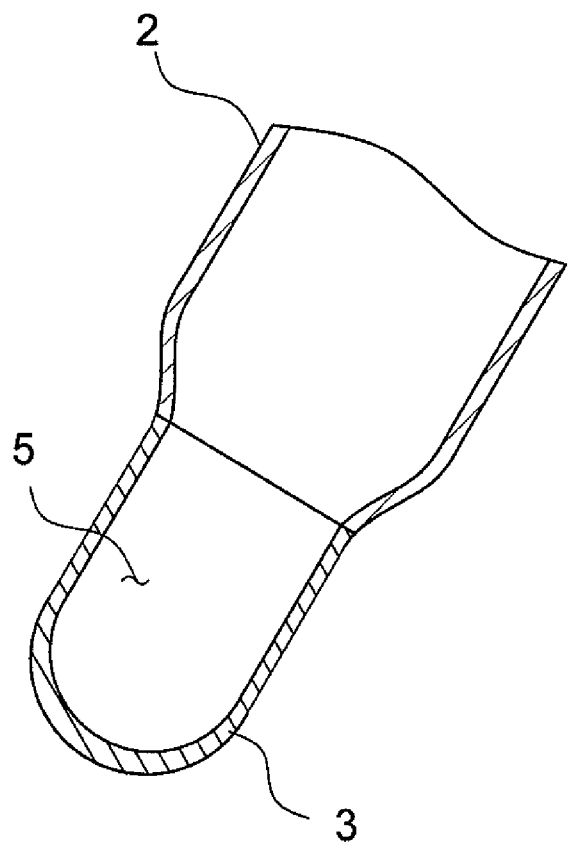
FIG. 2 is an enlarged view of proximity of the responsive glass membrane in FIG. 1.

The pH glass electrode 1 in accordance with this embodiment comprises, as shown in FIG. 1 and FIG. 2, a cylindrical tube 2 made of glass and a responsive glass membrane 3 connected to a distal end section of the cylindrical tube 2.

The cylindrical tube 2 houses an internal electrode 4 and is filled with internal fluid 5 as well. A lead wire 6 is connected to the internal electrode 4 and the lead wire 6 extends outside from a proximal end section of the cylindrical tube 2 so as to be connected to a pH meter, not shown in drawings.

The responsive glass membrane 3 is made of titanium-containing oxide glass containing 20~80 mol % of titanium dioxide and lithium oxide, and in a cylindrical shape with its distal end section substantially formed in hemisphere by means of blow molding. In order to connect the responsive glass membrane 3 to the cylindrical tube 2, titanium-containing oxide glass used for the responsive glass membrane 3 is molten in a furnace kept at, for example, one thousand and several hundred degrees, and a distal end section of the cylindrical tube 2 is immersed in the molten titanium-containing oxide glass, followed by drawing it up at a predetermined speed and then blowing it.

As mentioned above, the responsive glass membrane 3 is made of titanium-containing oxide glass containing 20~80 mol % of titanium dioxide and lithium oxide, and the titanium-containing oxide glass does not produce photocatalytic activity under an ordinary illumination in a laboratory or under natural light in the open air. However, if ultraviolet light is irradiated from a light source such as an LED, a hydrogen-discharge tube, a xenon discharge tube, a mercury lamp, a ruby laser, a YAG laser, an excimer laser and a dye laser, the photocatalytic activity is induced so as to degrade an attached organic matter due to the oxidizing properties and to produce a self cleaning function due to the superhydrophilic function as well so that the taint attached to the glass is easily detached.

Figure 3:
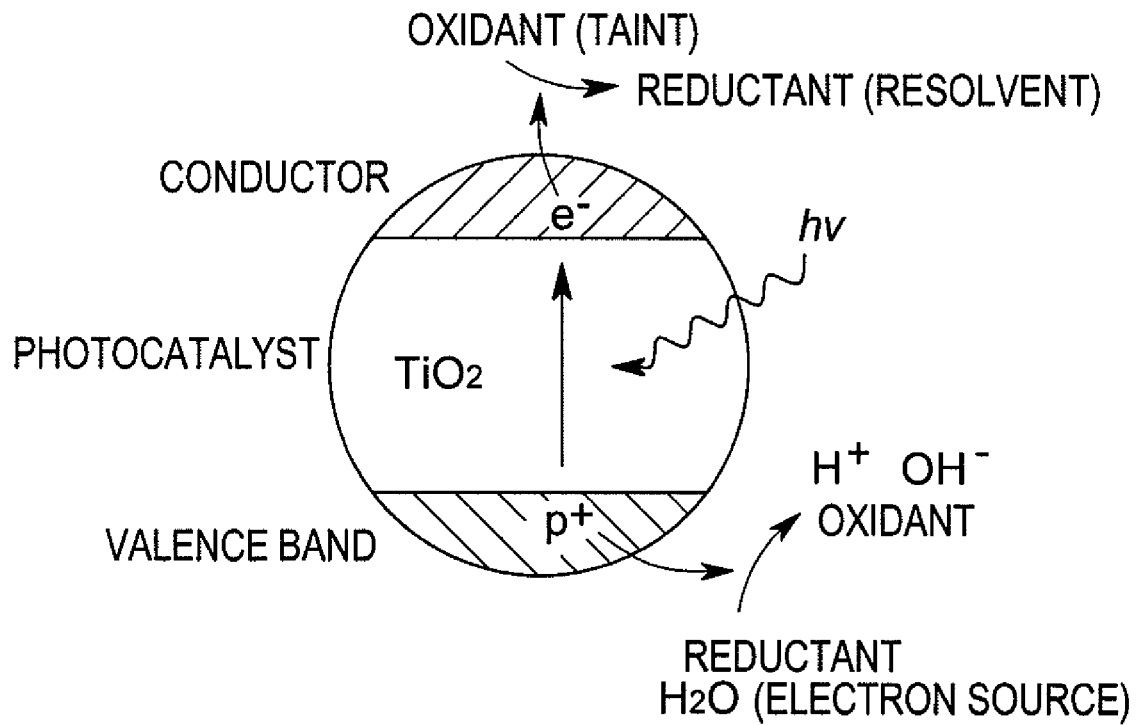
FIG. 3 is a conceptual diagram of oxidizing properties by photocatalytic activity.
Figure 4:
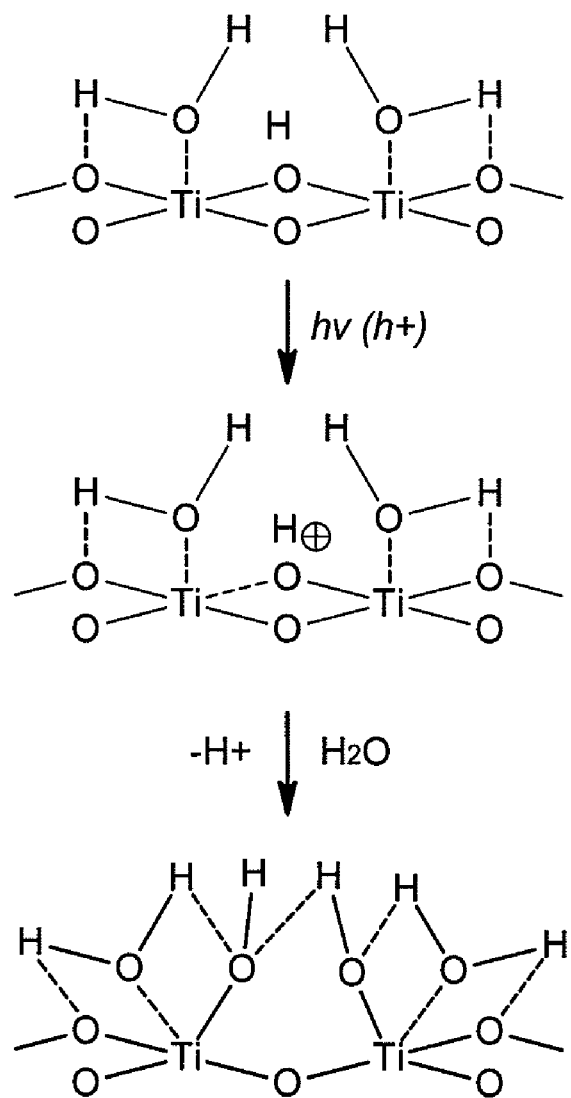
FIG. 4 is a conceptual diagram of superhydrophilic properties by photocatalytic activity.

A concept of an oxidation-reduction function due to the photocatalytic activity of titanium dioxide (semiconductor) is shown in FIG. 3. If the light whose energy is bigger than a bandgap is irradiated, the light is absorbed and an electron of a valence band is excited on a conduction band and an electron hole is generated on the valence band. Then if the excited electron moves to a chemical material located outside of the photocatalyst, the chemical material is reduced. If the electron hole moves, the chemical material is oxidized. In addition, a concept of the superhydrophilic function is shown in FIG. 4. Comparatively unstable hydroxyl is generated on a surface of oxidized titanium due to a reaction of the electron hole, which leads to produce the hydrophilic properties. Furthermore, an additional remark is that a hardness of the titanium dioxide increases if the light is irradiated.

The titanium-containing oxide glass to be a material of the responsive glass membrane 3 may either one of titanophosphate glass, titanosilicate glass and titanoborate glass, and titanophosphate glass containing 1~50 mol % of lithium oxide is preferable of all.

The glass having the composition shown in the following table 1 is experimentally produced as the responsive glass membrane 3.

TABLE 1

| Embodiment | Composition (mol %) | | | | Vitrify |
|---|---|---|---|---|---|
| | $Li_2O$ | $P_2O_5$ | $TiO_2$ | other | |
| 1 | 17 | 32 | 50 | 1 | ○ |
| 2 | 23 | 26 | 50 | 1 | ○ |
| 3 | 30 | 30 | 40 | — | ○ |

Figure 5:
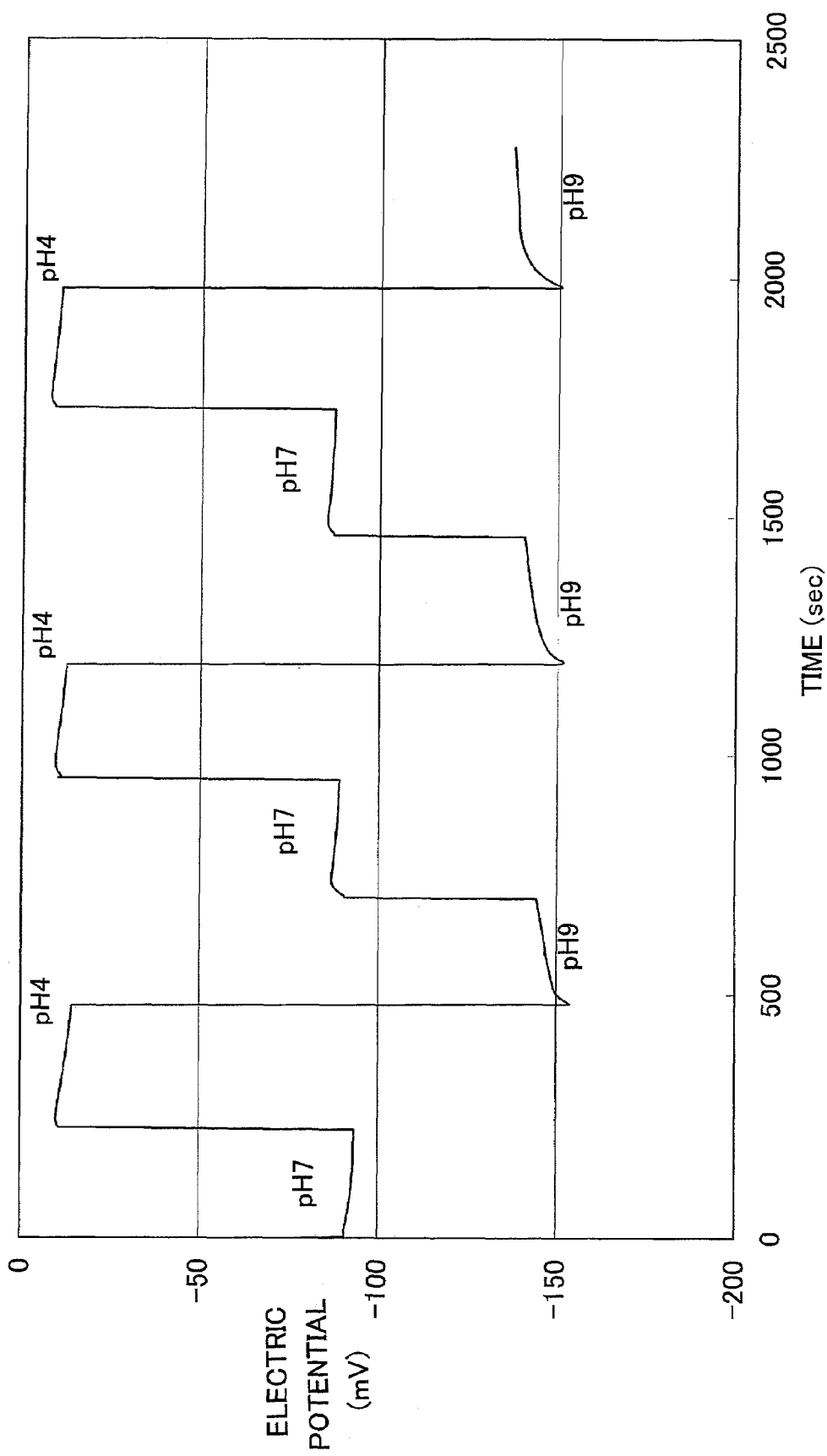
FIG. 5 is a graph showing a response of a pH glass electrode comprising a responsive glass membrane of $30Li_2O$-$30P_2O_5$-$40TiO_2$.

Either one of the examples of the responsive glass membrane 3 produces the self cleaning function and its resistance value is specific resistance $1.63 \times 10^7$ Ω·m, which is a value 2 digits lower than a resistance value of conventional lithium silicate glass even though the responsive glass membrane 3 contains titanium dioxide. In addition, the response of the pH glass electrode 1 comprising the responsive glass membrane 3 having a composition of the example 3 was examined. As a result, the pH glass electrode 1 also was superior in the pH response as shown by the graph in FIG. 5.

For example, a silver chloride electrode is used as the internal electrode 4, and, for example, a potassium chloride solution whose pH is adjusted to pH 7 is used as the internal solution 5.

In case of measuring the pH of a sample solution by the use of the pH glass electrode 1, the responsive glass membrane 3 of the pH glass electrode 1 is immersed in the sample solution whose pH is to be obtained, then an electro-motive force is generated for the responsive glass membrane 3 in accordance with a pH difference between the internal solution 5 and the sample solution. The pH is calculated by measuring the electro-motive force as a difference in potential (voltage) between the internal electrode 4 of the pH glass electrode 1 and an internal electrode of a reference electrode by the use of the reference electrode, not shown in drawings. Since the electro-motive force varies with the temperature, it is preferable to calculate the pH of the sample solution by correcting the difference in potential with an output signal value used as a parameter by the use of a temperature element and then to indicate the pH on a pH meter.

The present claimed invention is not limited to the above-mentioned embodiment.

The responsive glass membrane for ion selective electrode in accordance with this invention is not limited to the pH glass electrode 1, may be a combined electrode wherein a glass electrode and a reference electrode are integrally formed or a single electrode wherein a temperature compensated electrode is further integrated with the combined electrode.

Figure 6:
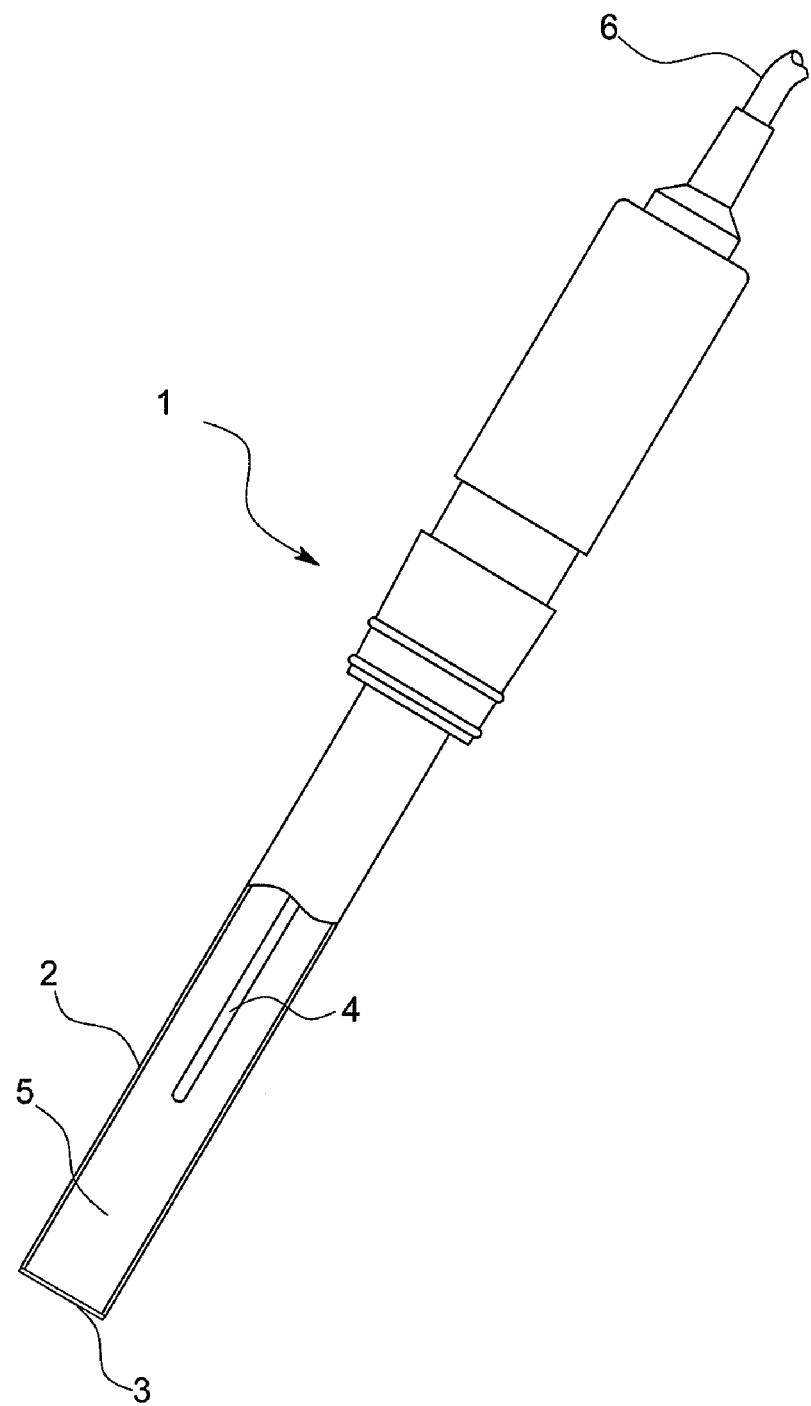
FIG. 6 is a partially broken view showing a part of an internal structure of a pH glass electrode in accordance with another embodiment of the present claimed invention.

For the ion selective electrode of this invention, the responsive glass membrane 3 is not limited to a shape of the cylindrical shape with its proximal end section substantially formed in hemisphere by means of blow molding, and the responsive glass membrane 3 may be manufactured by cutting and polishing a platy titanium-containing oxide glass. In addition, the responsive glass membrane 3 may be manufactured by molding the molten titan-containing oxide glass into a predetermined form. It is possible to manufacture a pH glass electrode 1 as shown in FIG. 6 by connecting thus manufactured responsive glass membrane 3 to an end opening section of the cylindrical tube 2 and sealing them by the use of an adhesive agent or a mechanical mechanism (a mechanical seal).

The light source for the ultraviolet rays may be arranged separately from the ion selective electrode of this invention, and the ion selective electrode of this invention itself may comprise a light source for the ultraviolet rays.

In addition, it is a matter of course that the present claimed invention may be variously modified without departing from a spirit of the invention.

In accordance with this invention, it is possible to wash the ion selective electrode without having an influence on the sample solution as being an object to be measured, thereby making it possible to conduct a stable and accurate measurement with less contamination or less influence of residual material. In addition, since there is no need of calibration for every measurement, continuous measurement can be conducted, and it is also possible to obtain a stable and accurate result even though the measurement is conducted continuously.

The invention claimed is:

1. An ion selective electrode comprising a responsive glass membrane made of oxide glass, wherein
    the oxide glass contains 20~80 mol% of titanium dioxide and lithium oxide.
2. The ion selective electrode described in claim 1, wherein
    the oxide glass is titanophosphate glass containing 1~50 mol% of lithium oxide.
3. The ion selective electrode described in claim 2, wherein the oxide glass is phosphate glass, silicate glass or borate glass.
4. The ion selective electrode described in claim 2, wherein the oxide glass contains cesium oxide.
5. The ion selective electrode described in claim 2, wherein the oxide glass contains oxidative product of a Group 3 element.
6. The ion selective electrode described in claim 2, wherein the oxide glass contains barium oxide.
7. The ion selected electrode described in claim 1, wherein the oxide glass is phosphate glass, silicate glass or borate glass.
8. The ion selective electrode described in claim 7, wherein the oxide glass contains cesium oxide.
9. The ion selective electrode described in claim 7, wherein the oxide glass contains oxidative product of a Group 3 element.

10. The ion selective electrode described in claim 7, wherein the oxide glass contains barium oxide.

11. The ion selective electrode described in claim 1, wherein the oxide glass contains cesium oxide.

12. The ion selective electrode described in claim 11, wherein the oxide glass contains oxidative product of a Group 3 element.

13. The ion selective electrode described in claim 11, wherein the oxide glass contains barium oxide.

14. The ion selective electrode described in claim 1, wherein the oxide glass contains oxidative product of a Group 3 element.

15. The ion selective electrode described in claim 14, wherein the oxide glass contains barium oxide.

16. The ion selective electrode described in claim 1, wherein the oxide glass contains barium oxide.

17. The ion selective electrode described in claim 1, wherein the oxide glass contains cesium oxide, oxidative product of a Group 3 element and barium oxide.

* * * * *